United States Patent [19]

Hirsch et al.

[11] Patent Number: 4,757,076

[45] Date of Patent: Jul. 12, 1988

[54] METHOD OF INHIBITING AROMATASE

[75] Inventors: Kenneth S. Hirsch, New Palestine; Harold M. Taylor, Indianapolis, both of Ind.

[73] Assignee: Eli Lilly and Company, Indianapolis, Ind.

[21] Appl. No.: 621,595

[22] Filed: Jun. 18, 1984

[51] Int. Cl.$^4$ .................... A61K 31/44; A61K 31/435
[52] U.S. Cl. .................... 514/277; 514/338; 514/357
[58] Field of Search ............... 424/263; 514/277, 357, 514/338

[56] References Cited

U.S. PATENT DOCUMENTS

| | | | |
|---|---|---|---|
| 2,727,895 | 12/1955 | Sperber et al. | 260/290 |
| 3,396,224 | 8/1968 | Van Heyningen | 424/263 |
| 3,397,273 | 8/1968 | Van Heyningen et al. | 424/263 |
| 3,655,359 | 4/1972 | Krumkalns et al. | 71/94 |
| 3,744,988 | 7/1973 | Krumkalns et al. | 71/78 |
| 3,794,656 | 2/1974 | Van Heyningen | 260/290 R |
| 4,116,665 | 9/1978 | Krumkalns | 71/66 |

OTHER PUBLICATIONS

Carter et al., Chemotherapy of Cancer, 2nd ed., pp. 361, 364 and 365 (1981).
U.S. Ser. No. 560,282, filed Dec. 12, 1983, by K. Hirsch et al.

*Primary Examiner*—Allen J. Robinson
*Attorney, Agent, or Firm*—Robert A. Conrad; Leroy Whitaker

[57] ABSTRACT

This invention provides a method of inhibiting aromatase and treating or preventing estrogen-dependent diseases in mammals by administering certain pyridine derivatives.

16 Claims, No Drawings

METHOD OF INHIBITING AROMATASE

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research*, supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide a method for inhibiting the enzyme aromatase in mammals employing certain pyridine derivatives. The invention thus provides for the treatment or prevention of breast cancer and other estrogen-dependent diseases.

SUMMARY OF THE INVENTION

This invention provides a method of inhibiting aromatase in mammals which comprises administering to said mammal an aromatase inhibiting amount of a pyridine of the formula

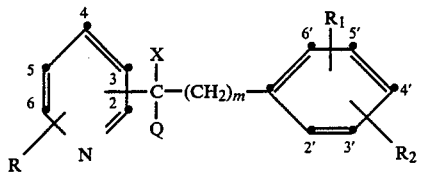

wherein
Q is hydrogen or

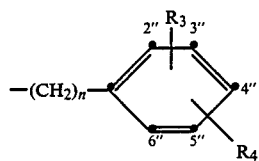

m and n are independently 0 or 1;

R is hydrogen or methyl;
$R_1$, $R_2$, $R_3$, and $R_4$ are independently hydrogen, methyl, $C_1$–$C_3$ alkoxy, halo, nitro, or trifluoromethyl, or when taken together, $R_1$ and $R_2$, and/or $R_3$ and $R_4$ are methylenedioxy; and
X is hydrogen, hydroxy, methyl, $C_1$–$C_3$ alkoxy, $C_1$–$C_3$ alkylthio, di-($C_1$–$C_3$alkyl)-amino, or halo, with the proviso that whenever one or both of m or n is 1, the benzene ring to which the respective methylene group is attached must be substituted by at least one substituent other than hydrogen, or a pharmaceutically acceptable salt thereof.

By virtue of their ability to inhibit the enzyme aromatase, the pyridines of the above formula are useful in the treatment and prevention of estrogen-dependent diseases, especially breast cancer, in mammals.

DETAILED DESCRIPTION AND PREFERRED EMBODIMENT

The term "$C_1$–$C_3$ alkoxy" refers to methoxy, ethoxy, propoxy, and isopropoxy. The term "$C_1$–$C_3$ alkyl" refers to methyl, ethyl, propyl, and isopropyl. The term "halo" refers to fluoro, chloro, bromo, and iodo.

A preferred group of compounds useful in the method of this invention are those wherein:
(a) one of $R_1$ and $R_2$ is fluoro or chloro,
(b) Q is substituted phenyl and one of $R_3$ and $R_4$ is fluoro or chloro,
(c) X is hydroxy or hydrogen,
(d) the pyridine ring is substituted with the diarylmethyl group in the 4- or preferably the 3-position,
(e) m is 0,
(f) n is 0, and
(g) R is hydrogen.

Especially preferred compounds are those wherein R is hydrogen, m and n are both zero, X is hydrogen or hydroxy, one of $R_1$ and $R_2$ is fluoro or chloro in the 4'-position and one of $R_3$ and $R_4$ is fluoro or chloro in the 4''-position.

The most preferred compounds are 3-bis(4-chlorophenyl)-3-methylpyridine and α,α-bis(4-chlorophenyl)-3-pyridinemethanol and their pharmaceutically acceptable salts.

The compounds used in this invention are disclosed and/or can be prepared by the methods described in U.S. Pat. Nos. 3,396,224 and 2,727,895. Both patents are expressly incorporated in this application by reference. The compounds as disclosed in the patents are described as being useful as fungicides, bactericides, and anticonvulsants. The patents do not disclose any utility related to the inhibition of aromatase or the treatment of estrogen-dependent diseases.

As will be recognized by those skilled in the art, except when the phenyl groups are identically substituted, the compounds used in this invention contain an asymmetric carbon atom. This invention is not limited to any particular isomer but includes the individual enantiomers as well as the racemates of the compounds.

The pharmaceutically acceptable acid addition salts of the pyridines used in this invention can be prepared employing those acids of sufficient acidity to form acid addition salts with the weakly basic pyridine group. These include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

The compounds used in the method of this invention are useful in preventing or therapeutically treating estrogen-dependent diseases, including breast cancer, in mammals by virtue of their ability to inhibit the enzyme aromatase. Their ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2-[$^3$H]-androstenedione, the microsomes and a NADPH generating system. The concentrations of the inhibitors tested ranged between 0.005 and 10 μM. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity (EC$_{50}$) when the concentration of substrate (androstenedione) is 0.1 μM. The EC$_{50}$'s of certain of the compounds of the above formula are summarized in Table 1.

TABLE 1

| Aromatase Inhibition in the Rat Ovarian Microsome Assay | |
|---|---|
| Compound | EC$_{50}$* |
| 3-bis(4-chlorophenyl)methylpyridine | 0.084 |
| 2-bis(4-chlorophenyl)methylpyridine | 4.4 |
| α-(4-chlorobenzyl)-α-(4-chlorophenyl)-3-pyridinemethanol | 2.9 |
| α-(3,4-dichlorobenzyl)-α-(4-chlorophenyl)-3-pyridinemethanol | 3.15 |
| α,α-bis(4-chlorophenyl)-3-pyridinemethanol | 0.15 |
| α-(2,4-dichlorobenzyl)-α-(4-chlorophenyl)-3-pyridinemethanol | 3.2 |
| α,α-bis(3-chlorophenyl)-3-pyridinemethanol | 4.5 |
| α,α-bis(3-chlorophenyl)-3-pyridinemethanol hydrochloride | 3.7 |
| α,α-bis(4-chlorophenyl)-4-pyridinemethanol hydrochloride | 0.084 |
| 4-bis(4-chlorophenyl)methylpyridine hydrochloride | 0.16 |
| α-(4-chlorophenyl)-α-(3-trifluoromethylphenyl)-3-pyridinemethanol hydrochloride | 0.65 |
| 1,2-bis(4-chlorophenyl)-1-(4-pyridyl)ethanol | 0.185 |
| α-(3-pyridyl)-4-chlorobenzyl alcohol | 2.40 |
| 4-(4-nitrobenzyl)pyridine | 0.98 |
| α-(4-chlorophenyl)-N,N—di(n-propyl)-3-pyridylmethylamine | 0.15 |
| α,α-bis(3-bromophenyl)-3-pyridinemethanol | 2.2 |
| α-(2-methoxy-4-chlorophenyl)-α-phenyl-3-pyridinemethanol | 1.8 |
| α-(2,4-dichlorobenzyl)-α-(4-chlorophenyl)-3-pyridinemethanol hydrochloride | >5.0 |
| α-(2-chlorophenyl)-α-(4-chlorophenyl)-3-pyridinemethanol hydrochloride | 2.2 |
| α,α-bis(2,4-dichlorobenzyl)-3-pyridinemethanol hydrochloride | 1.85 |
| α-(4-chlorophenyl)-α-phenyl-3-pyridinemethanol | 2.05 |
| α-(4-chlorophenyl)-α-(3,4-methylenedioxyphenyl)-3-pyridinemethanol | 0.5 |
| α-(4-chlorobenzyl)-α-(3-chlorophenyl)-3-pyridinemethanol | 3.2 |
| α,α-bis(4-methoxyphenyl)-3-pyridinemethanol | >5.0 |
| α-(2,4-dichlorophenyl)-α-(4-fluorophenyl)-3-pyridinemethanol hydrochloride | 0.315 |
| α-(4-methylphenyl)-α-phenyl-3-pyridinemethanol | 2.4 |
| 3-[bis(4-chlorophenyl)chloromethyl]pyridine hydrochloride | 0.20 |
| 4-bis(2-chlorophenyl)methylpyridine | 0.49 |
| 4-(4-chlorobenzyl)pyridine | 0.55 |
| α-(4-chlorophenyl)-α-(4-methylphenyl)-3-pyridinemethanol hydrochloride | 0.23 |
| α,α-bis(4-chlorobenzyl)-3-pyridinemethanol | >5.0 |
| α-(4-chlorobenzyl)-α-(2,4-dichlorobenzyl)-3-pyridinemethanol | 2.4 |
| α,α-bis(2,4-dichlorophenyl)-3-pyridinemethanol hydrochloride | 4.0 |
| α-(2,4-difluorophenyl)-α-phenyl-3-pyridinemethanol | 2.05 |
| α-(2,4-dichlorophenyl)-α-phenyl-3-pyridinemethanol | >5.0 |
| α-(4-chlorophenyl)-5-methyl-α-phenyl-3-pyridinemethanol | 4.1 |
| α,α-bis(4-chlorophenyl)-3-pyridylmethyl-methylether hydrochloride | 1.6 |
| α,α-dibenzyl-3-pyridinemethanol | 2.85 |
| 3-[α-methyl-α,α-bis(4-chlorophenyl)methyl]pyridine hydrochloride | 0.145 |
| α,α-bis[4-(dimethylamino)phenyl]-4-pyridinemethanol | 3.4 |
| 3-[α-(4-chlorophenyl)-α-(n-propylthio)-4-chlorobenzyl]pyridine | 1.75 |
| 3-[bis(4-chlorophenyl)fluoromethyl]pyridine | 0.20 |

*Concentration of compound in μM required to achieve 50% inhibition of aromatase activity when substrate concentration is 0.1 μM.

By virtue of their ability to inhibit the enzyme aromatase, the compounds to be employed in the method of this invention are able to inhibit the synthesis of estrogens in mammals, thereby making the compounds useful in the treatment of estrogen-dependent diseases, such as breast cancer. This in vivo activity was demonstrated in the following test systems.

Estrogen Synthesis Inhibition in Rats

Immature female Wistar rats (45–55 grams) were divided into control and test groups of 4–8 animals each. Test compounds were administered for seven days as a component of the diet. Control animals received diet without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of 3:1 (v/v) saline-ethanol.

After two hours, the animals were killed by decapitation. Uteri were isolated, trimmed of extraneous connective tissue, and weighed. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls.

Ovaries from rats treated with [$^3$H]-testosterone were excised, cleaned of extraneous tissue, and homogenized in 2.5 ml of a 1.0 mM potassium phosphate buffer containing 3.0 mM $MgCl_2.6H_2O$, 320 mM sucrose, and 0.25% Triton X-100 (polyethylene glycol p-isooctyl phenyl ether, Rohm and Haas) at pH 6.5. The ovarian steroids were extracted with 1.5 ml of 9:1 (v/v) toluene/ethanol to which had been added 25 to 100 mcg. each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded, and the pellet was dissolved in 0.3 N potassium hydroxide. Protein was determined according to the method of Bradford, *Analytical Biochemistry*, 72, 248 (1976).

The organic residue from each above extraction was redissolved in 9:1 (v/v) dichloromethane/methanol. The solution of each sample was applied to separate silica gel thin layer chromatography plates which contained a fluorescent indicator. The plates were developed in the first dimension with 160:38:1.5:0.5 (v/v/v/v) dichloromethane/ethyl acetate/methanol/acetic acid to within 3 cm of the top of the plate. After air-drying, the plate was developed in the second dimension with 180:19:1 (v/v/v) dichloromethane/methanol/ammonium hydroxide. The plate was air-dried and viewed under 254 nm UV light.

The visible spots were marked, and the plates were sprayed with primulin (0.001% in 4:1 v/v acetone/water) according to the method of Wright, J. Chromatography, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry. Corrections were made based on the recoveries of the [$^{14}$C]-steroid. Steroid concentrations are expressed as femtomoles per milligram protein.

TABLE 2

| Test No. | Compound | Effects of Compounds on estrogen levels and uterine weight | | | | | |
|---|---|---|---|---|---|---|---|
| | | Dose* | Animals | Mean Uterine Weight (mg) | Mean Steroid Concentration** | | |
| | | | | | estradiol | estrone | estriol |
| I | α,α-bis(4-chlorophenyl)-3-pyridinemethanol | 30 | 4 | 127.25+ | 1.04 | 0.19+ | 0.70 |
| | | 300 | 5 | 87.80+ | 0.36+ | 0.10+ | 0.39 |
| | testosterone-treated control | — | 8 | 163.88 | 1.29 | 0.31 | 0.68 |
| | Corn oil control | — | 6 | 54.17+ | — | — | — |

*ppm in feed. 300 ppm corresponds to approximately 30 mg/kg/day; 30 ppm corresponds to approximately 3 mg/kg/day.
**femtomoles per milligram of protein.
+significantly different from testosterone-treated control, $p < 0.05$.

DMBA-Induced Mammary Tumor Inhibition

Mammary tumors were produced in female Sprague-Dawley rats which were 50-60 days old by the gavage administration of 20 mg of 7,12-dimethylbenz[a]anthracene (DMBA). About six weeks after DMBA administration, the mammary glands were palpated at weekly intervals for the appearance of tumors. Whenever one or more tumors appeared and were measurable in an animal, that animal was selected for experimentation. An attempt was made to uniformly distribute the various sizes of tumors in the treated and control groups such that one group did not start with rats having tumors which, on the average, were significantly larger than those of any other group. Each control and test group contained 8 animals. The test compound was administered mixed into the food at a concentration of 300 ppm (corresponding to an appropriate daily dose of 30 mg/kg). The experiment included a group of control rats having tumors and were given food without the compound admixed. The tumors were measured at the start of the experiments and generally had an area of approximately 15-100 mm$^2$. The area of each tumor was calculated by multiplying the shortest and longest diameters of the tumor. The treatment and measurement of animals continued for 5 weeks at which time the final areas of the tumors were determined. The results of these tests are shown in Table 3 below.

TABLE 3

| | | Anti-Tumor Activity | | | |
|---|---|---|---|---|---|
| | | | Duration | Mean Tumor Area (mm$^2$) | |
| Test No. | Compound | Dose* | of Test | Start | Finish |
| I | Control | — | 5 weeks | 73.9 | 1140 |
| | α,α-bis(4-chlorophenyl)-3-pyridinemethanol | 300 ppm | | 108.8 | 433 |

*Dosed in the diet. 300 ppm corresponds to approximately 30 mg/kg/day.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of the above formula.

Such pharmaceutical compositions comprise as active ingredient a compound of the above formula associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

We claim:

1. A method of inhibiting aromatase in a mammal which comprises administering to said mammal an aromatase inhibiting amount of a compound of the formula

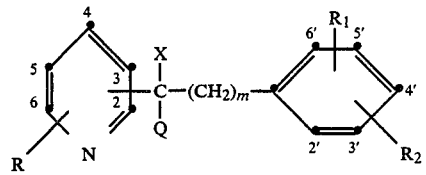

wherein:

Q is hydrogen or

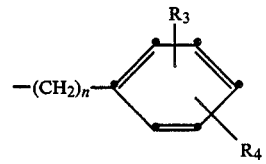

m and n are independently 0 or 1;

R is hydrogen or methyl;

$R_1$, $R_2$, $R_3$, and $R_4$ are independently hydrogen, methyl, $C_1$–$C_3$ alkoxy, halo, nitro, or trifluoromethyl, or when taken together, $R_1$ and $R_2$, and/or $R_3$ and $R_4$ are methylenedioxy; and X is hydrogen, hydroxy, methyl, $C_1$–$C_3$ alkoxy, $C_1$–$C_3$ alkylthio, di-($C_1$–$C_3$alkyl)amino, or halo, with the proviso that whenever one or both of m or n is 1, the benzene ring to which the respective methylene group is attached must be substituted by at least one substituent other than hydrogen, or a pharmaceutically acceptable salt thereof.

2. The method according to claim 1 employing a compound wherein one of $R_1$ and $R_2$ is fluoro or chloro.

3. The method according to claim 2 employing a compound wherein Q is substituted phenyl and one of $R_3$ and $R_4$ is chloro or fluoro.

4. The method according to claim 3 employing a compound wherein the chloro or fluoro substituents are in the 4'- and 4"-positions.

5. The method according to claim 4 employing a compound wherein X is hydrogen.

6. The method according to claim 4 employing a compound wherein X is hydroxy.

7. The method according to claim 5 wherein the compound employed is 3-bis(4-chlorophenyl)methylpyridine or a pharmaceutically acceptable salt thereof.

8. The method according to claim 6 wherein the compound employed is α,α-bis(4-chlorophenyl)-3-pyridinemethanol or a pharmaceutically acceptable salt thereof.

9. A method of treating estrogen-dependent diseases in a mammal which comprises administering to said mammal an effective amount of a compound according to the formula

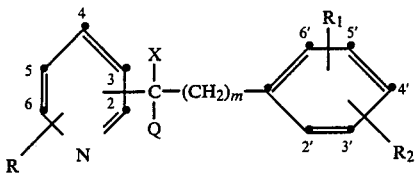

wherein:

Q is hydrogen or

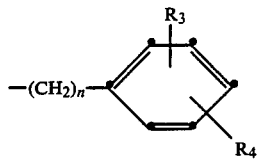

m and n are independently 0 or 1;

R is hydrogen or methyl;

$R_1$, $R_2$, $R_3$, and $R_4$ are independently hydrogen, methyl, $C_1$-$C_3$ alkoxy, halo, nitro, or trifluoromethyl, or when taken together, $R_1$ and $R_2$, and/or $R_3$ and $R_4$ are methylenedioxy; and X is hydrogen, hydroxy, methyl, $C_1$-$C_3$ alkoxy, $C_1$-$C_3$ alkylthio, di($C_1$-$C_3$ alkyl)amino, or halo, with the proviso that whenever one or both of m or n is 1, the benzene ring to which the respective methylene group is attached must be substituted by at least one substituent other than hydrogen, or a pharmaceutically acceptable salt thereof.

10. The method according to claim 9 employing a compound wherein one of $R_1$ and $R_2$ is chloro or fluoro in the 4'-position, Q is substituted phenyl, and one of $R_3$ and $R_4$ is fluoro or chloro in the 4''-position.

11. The method according to claim 10 employing a compound wherein X is hydrogen or hydroxy.

12. The method according to claim 11 wherein the compound employed is 3-bis(4-chlorophenyl)methylpyridine or a pharmaceutically acceptable salt thereof.

13. The method according to claim 11 wherein the compound employed is α,α-bis(4-chlorophenyl)-3-pyridinemethanol or a pharmaceutically acceptable salt thereof.

14. The method according to claim 9 wherein the estrogen-dependent disease is breast carcinoma.

15. The method according to claim 14 wherein the compound employed is 3-bis(4-chlorophenyl)methylpyridine or a pharmaceutically acceptable salt thereof.

16. The method according to claim 14 wherein the compound employed is α,α-bis(4-chlorophenyl)-3-pyridinemethanol or a pharmaceutically acceptable salt thereof.

* * * * *